US009814521B2

(12) United States Patent
Geistert

(10) Patent No.: US 9,814,521 B2
(45) Date of Patent: Nov. 14, 2017

(54) ABLATION CATHETER ARRANGEMENT AND METHOD FOR TREATMENT OF A CARDIAC ARRHYTHMIA

(75) Inventor: Wolfgang Geistert, Rheinfelden (DE)

(73) Assignee: VASCOMED GMBH (DE)

( * ) Notice: Subject to any disclaimer, the term of this patent is extended or adjusted under 35 U.S.C. 154(b) by 1543 days.

(21) Appl. No.: 12/987,188

(22) Filed: Jan. 10, 2011

(65) Prior Publication Data
US 2011/0172657 A1 Jul. 14, 2011

(51) Int. Cl.
A61B 18/14 (2006.01)
(52) U.S. Cl.
CPC .... A61B 18/1492 (2013.01); A61B 2218/002 (2013.01)
(58) Field of Classification Search
CPC ............... A61B 2218/002; A61B 18/1492
USPC ...................................... 606/41, 45
See application file for complete search history.

(56) References Cited

U.S. PATENT DOCUMENTS

| 6,514,249 B1 | 2/2003 | Maguire et al. | |
| 2001/0039415 A1* | 11/2001 | Francischelli | A61B 18/1402 606/27 |
| 2003/0204186 A1 | 10/2003 | Geistert | |
| 2003/0204187 A1 | 10/2003 | Hintringer et al. | |
| 2007/0100232 A1 | 5/2007 | Hiller et al. | |
| 2008/0161794 A1 | 7/2008 | Wang et al. | |
| 2009/0326526 A1 | 12/2009 | Ingle et al. | |

FOREIGN PATENT DOCUMENTS

| WO | WO 2004064657 A2 | 8/2004 |
| WO | WO 2009158595 A1 | 12/2009 |

OTHER PUBLICATIONS

European Search Report (dated May 16, 2011).

* cited by examiner

Primary Examiner — Michael Peffley
Assistant Examiner — Samantha Good
(74) Attorney, Agent, or Firm — Craig A. Fieschko; DeWitt Ross & Stevens S.C.

(57) ABSTRACT

An ablation catheter arrangement includes an ablation generator, a rinsing liquid source for providing a liquid for rinsing the treatment area in which ablation is performed, and an ablation catheter connectable to the ablation generator and to the rinsing liquid source. The ablation catheter has an ablation area, at least one rinsing opening, and a rinsing bath for supplying rinsing liquid to the treatment area. A blood pressure measurement device detects the intracardiac blood pressure over the liquid column of the rinsing liquid, and communicates with the rinsing channel of the ablation catheter by fluid connection.

22 Claims, 5 Drawing Sheets

ABLATION CATHETER ARRANGEMENT AND METHOD FOR TREATMENT OF A CARDIAC ARRHYTHMIA

CROSS-REFERENCE TO RELATED APPLICATIONS

This application claims priority under 35 USC §119(e) to U.S. Provisional Patent Application 61/294,116, filed on Jan. 12, 2010, which is hereby incorporated by reference in its entirety.

FIELD OF THE INVENTION

The invention relates to an ablation catheter arrangement for ablation of cardiac tissue for treatment of a cardiac arrhythmia, in particular atrial fibrillation or flutter, having an ablation generator for supplying ablation energy; an ablation catheter, which has a rinsing channel for connection to a rinsing liquid source for supplying a liquid for rinsing the treatment area; and a blood pressure measurement device. It also relates to a method for treatment of a cardiac arrhythmia, in particular atrial fibrillation or flutter, by ablation of cardiac tissue.

BACKGROUND OF THE INVENTION

It has long been known that cardiac arrhythmias can be treated by targeted erosion of cardiac tissue and of the conduction pathways contained therein, with such erosion being referred to as ablation. Current ablation methods include HF and RF ablation, cryoablation, laser ablation, microwave ablation, and ablation with focused ultrasound.

The HF generators used in routine clinical practice today generate a high-frequency alternating current, typically 500 kHz. A local heating effect is created by contacting tissue with the ablation catheter, to which the high-frequency signal is applied for the duration of the ablation process. This results in temperatures between 45° C. and 100° C. The result is a tissue lesion, usually having a maximum diameter of 5 mm and a depth of up to 2-3 mm. The goal of the lesion is to eliminate the previously identified arrhythmogenic substrate which is responsible for the tachycardia mechanism.

In cryoablation, the myocardial tissue responsible for the arrhythmia is supercooled in a targeted manner. Cold has been used for many decades for treating cardiac arrhythmias. Since cryotherapy freezes the cells—in contrast with the heat-based radiofrequency ablation mentioned above—it constitutes an alternative treatment option for electro-physiologists and heart surgeons.

The tip of the cryoablation catheter is cooled down to temperatures below 0° C. Heat is withdrawn from the surrounding tissue via the tip of the catheter. Depending on the catheter used, temperatures of −75° C. or even lower occur at the tip of the catheter. The patient does not perceive this cold. The myocardial cells responsible for conduction of the arrhythmia are altered by the influence of cold in such a way that they can no longer conduct the electric stimulation.

During a cardiological ablation procedure, it is necessary to check regularly, or better yet continuously, to ascertain whether the cardiac arrhythmia to be treated has been eliminated. Traditionally the success of the treatment is monitored by means of an ECG measurement and/or by intracardiac blood pressure measurement. The blood pressure measurement is of benefit in particular in ablation of tachycardiac atrial arrhythmias (atrial fibrillation, atrial flutter) because by measuring the blood pressure in the atrium, it is easy to ascertain whether the pumping function of the atria has been restored. The blood pressure measurement device is a device in addition to the traditional ablation arrangement (the ablation device and optional ECG measurement device), and requires an additional blood pressure measurement catheter placed in the atria. This blood pressure measurement catheter is necessary because the low atrial pressures cannot be measured with a traditional external blood pressure measurement.

FIG. 1 shows a device and catheter arrangement for HF catheter ablation of the traditional type. In addition to the ablation catheter 1, at least one additional EP diagnostic catheter 2 and a blood pressure measurement catheter 3 are placed in the heart of the patient 4. The ablation catheter 1 and the EP diagnostic catheter 2 are connected to an ECG measurement system 5. The ablation catheter 1 has rinsing openings, which are intended to allow liquid to be dispensed to the ablation site to cool the tissue at this site. The rinsing openings are connected to a rinsing liquid conduit 6, which is connected at its proximal end to a pump 7, which ensures the supply of liquid from a reservoir 8.

The blood pressure measurement catheter 3 is connected to a blood pressure measurement device 9. Blood pressure changes are carried outward and measured with the blood pressure measurement device 9 via the liquid column in the blood pressure measurement catheter 3.

FIG. 2 shows an atrial blood pressure curve during a sinus rhythm (a) and curves during atrial fibrillation and/or flutter (b)+(c). This shows clearly that the difference allows simple monitoring of the success of ablation.

SUMMARY OF THE INVENTION

One object of the invention is to provide a simplified ablation catheter arrangement for treatments such as those mentioned above, which allows simpler and more rapid insertion is into a patient's body, and simpler handling during a procedure. The invention also provides a simplified ablation method of the type mentioned above.

In one version of the invention, an ablation catheter can be connected to the ablation generator and the rinsing liquid source. The ablation catheter has an ablation area, at least one rinsing opening, and a rinsing channel for supplying rinsing liquid into the treatment area. In addition, it includes a blood pressure measurement device designed for detection of the intracardiac blood pressure via the liquid column of the rinsing liquid, and in fluid connection with the rinsing channel of the ablation catheter. Direct connection of the blood pressure measurement device to the ablation catheter simplifies the arrangement, allowing omission of the separate blood pressure measurement catheter and the complexity associated with providing it, inserting it, handling it, removing it from the body, and properly disposing of it.

The rinsing channel of the ablation catheter may be a liquid channel that is already provided for other purposes. In the case of HF ablation catheters, it may be a liquid channel through which cooling liquid is passed to the treatment area. With all ablation catheters, this may be a liquid channel through which a guide wire may be advanced, serving to control the ablation catheter and/or to guide the ablation area of the ablation catheter to the treatment area.

With a traditional device and catheter arrangement, an ECG measurement device may also be provided, but this may be omitted in the case of a purely anatomical therapeutic approach.

In one version of the invention, the rinsing liquid source has a rinsing liquid pump and a conveyor/measuring control unit for controlling the flow of rinsing liquid over time, and which allows measurement of the blood pressure. As an alternative to use of a pump, the rinsing liquid could be conveyed manually or by gas pressure, for example, and then it might be possible to refrain from using the control unit mentioned above. However, where the control unit is provided, it may be integrated into the rinsing liquid pump. In additional versions, the control unit may be integrated into the blood pressure measurement device, or may be provided as a separate unit connectable to the rinsing liquid pump and the blood pressure measurement device via data communication means, in particular signal lines. The various versions of the invention mentioned above may each have their own advantages in particular circumstances, e.g., simplification of handling with structural integration of multiple components, or greater flexibility where components are separately provided (in which case components can be chosen and assembled as needed).

Another version of the invention is provided with a branched rinsing liquid conduit for permanent fluid connection of the ablation catheter to the blood pressure measurement device and to the rinsing liquid source, in particular the rinsing liquid pump. The tube permanently connects the rinsing liquid pump and the blood pressure measurement device in the use state to the proximal end of the ablation catheter by both mechanical and fluid connections. During use, a permanent cohesive liquid column of rinsing liquid is present in the individual portions of the tube.

In an alternative version, the rinsing liquid conduit is provided with a reversing valve device (e.g., a two-way valve) for establishing an alternating temporary fluid connection of the ablation catheter to the blood pressure measurement device or to the rinsing liquid source, in particular the rinsing liquid pump.

Due to the reversing valve device, the liquid column formed in the catheter itself is coupled by fluid flow either to the rinsing liquid source or to the blood pressure measurement device to implement either supply of the rinsing liquid, or measurement of blood pressure. Thus, since the rinsing liquid pump is separated from the end of the ablation catheter at the valve end, no special operational control of the pump is necessary to be able to perform blood pressure measurements.

In another version, the supply/measurement control unit may be integrated with any one or more of the rinsing liquid pump, the blood pressure measurement device, and the branched tube for rinsing liquid, and the reversing valve mechanism.

In addition, an ECG measurement device may also be provided with the ablation catheter arrangement for recording cardiac action potentials that are picked up by sensors.

In another version of the invention, an ablation evaluation unit is connected at the input end to the blood pressure measurement device and/or to the ECG measurement device, is preferably being integrated into the design together with the ECG measurement device and/or the blood pressure measurement device (and especially preferably with both devices).

BRIEF DESCRIPTION OF THE DRAWINGS

Further features and advantages of the invention will be apparent from the following description in connection with the drawings, wherein.

DETAILED DESCRIPTION OF EXEMPLARY VERSIONS OF THE INVENTION

Figure 1:
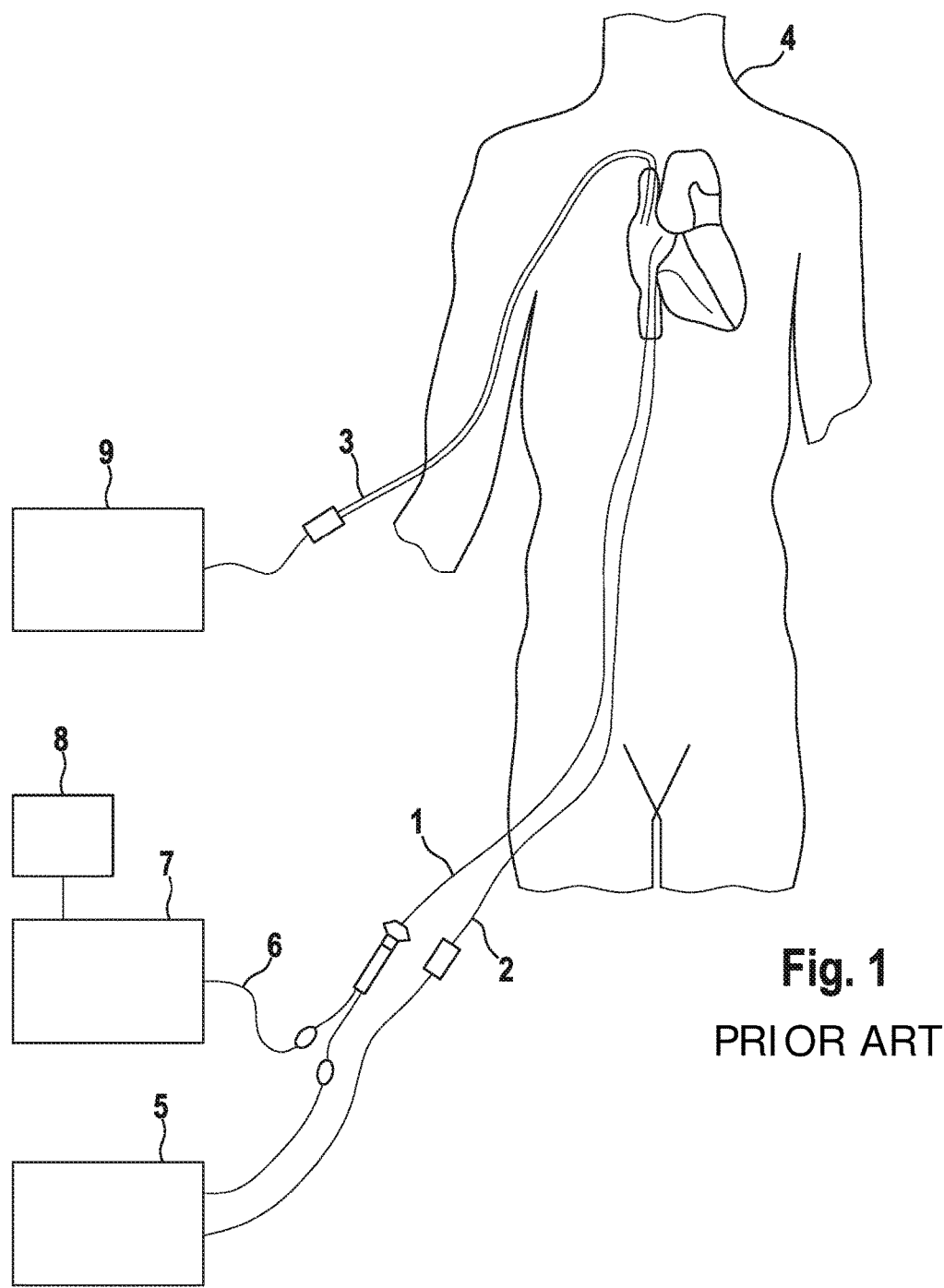
FIG. 1 shows a schematic diagram of a traditional ablation catheter arrangement in a schematic diagram.
Figure 2:
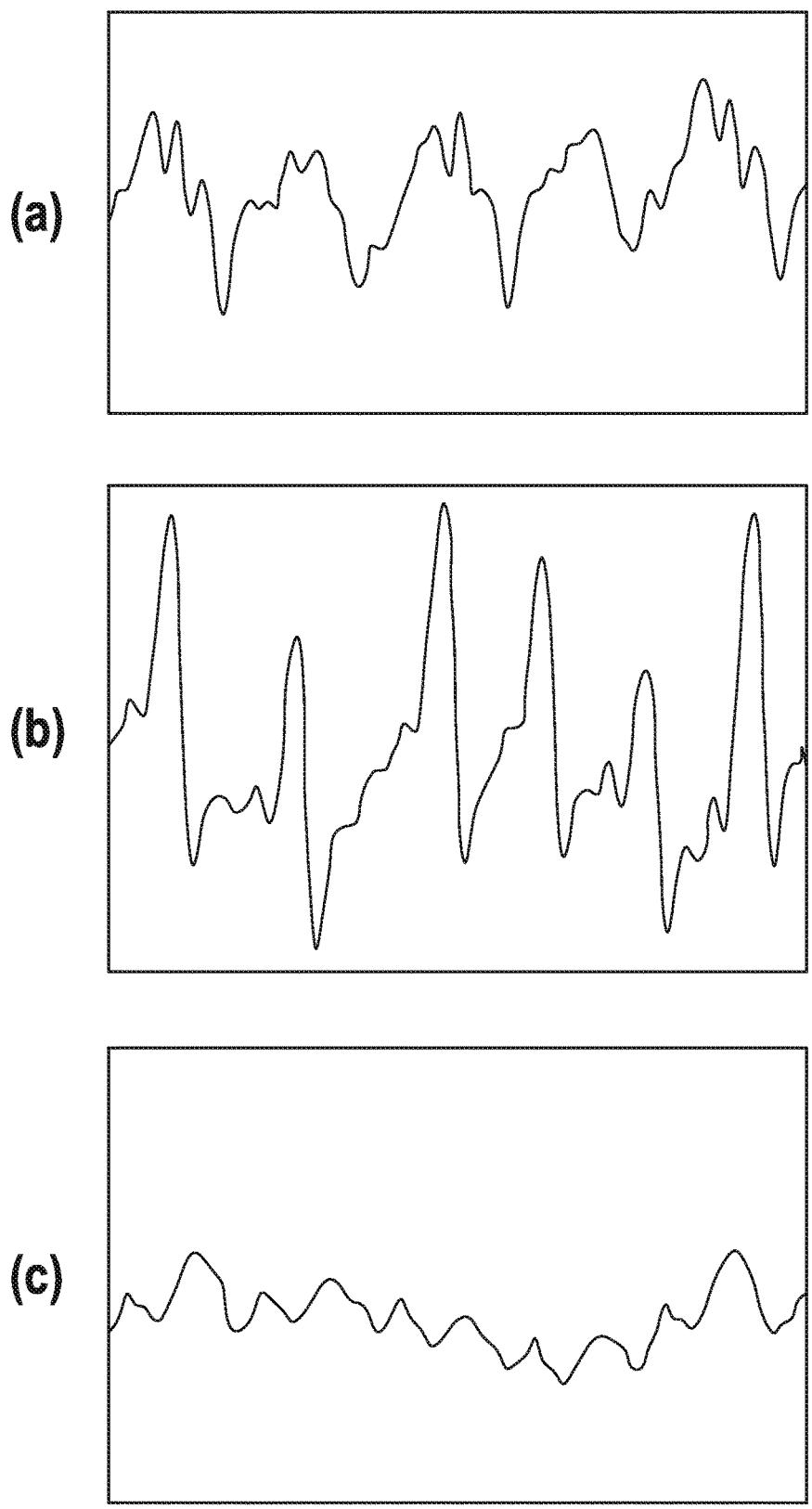
FIG. 2 shows comparative diagrams of atrial blood pressure curves in various arrhythmia states.
Figure 3:
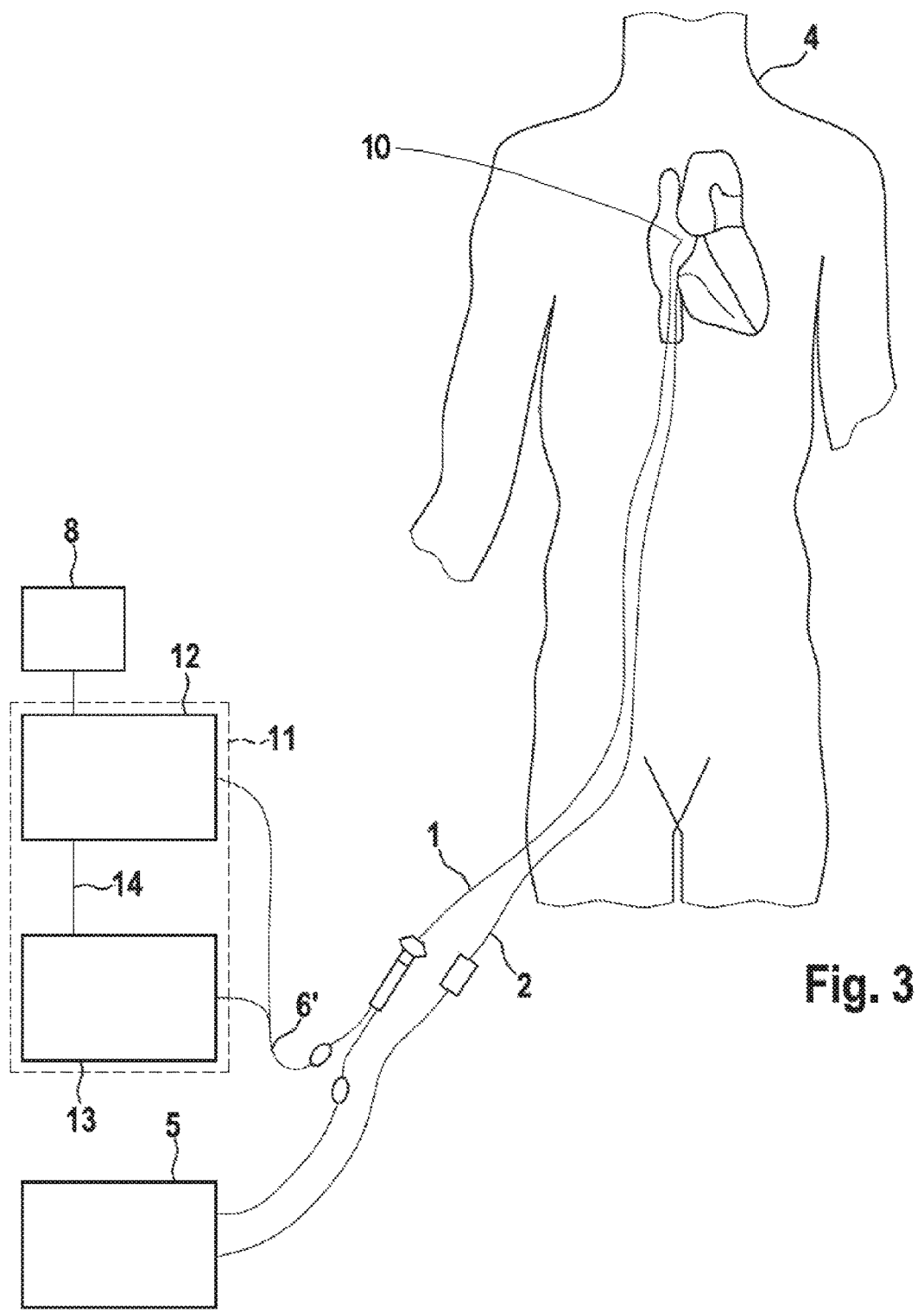
FIG. 3 shows a schematic diagram of a first version of the invention.

FIG. 3 shows an exemplary version of the invention, laid out similarly to FIG. 1, and using the same reference numerals as used in FIG. 1. The rinsing liquid connection of the ablation catheter 1 is connected to a device and/or an assembly 11 which contains a pump 12 and a blood pressure measurement device 13. These may be two separate devices, or they may be one device with two subassemblies. A modified rinsing liquid conduit 6' is divided in the form of a Y and connects a rinsing aperture 10 and the liquid column in the ablation catheter 1 to the pump 12 and also to the blood pressure measurement device 13. It is then possible to simultaneously convey liquid and measure the blood pressure.

To allow a blood pressure measurement to be performed simultaneously with liquid supply, the pump 12 sends a message to the blood pressure measurement device 13 via a data line 14 and a corresponding control input on the measurement device. The message dictates when and (if necessary) in which amount and in which manner (e.g., continuous, surge-like, wave-form and/or temperature-dependent pressure) the pump 12 shall deliver fluid. Very sensitive blood pressure measurements may be performed where the pump 12 sets the supply at the moment of the blood pressure measurement. In another version of the invention, the alternating pumping and blood pressure measurement are coordinated by means of a separate control unit (not shown in FIG. 1) utilizing the data line 14, or by a control unit installed either in the pump 12 or in the blood pressure measurement device 13.

The pump 12, the blood pressure measurement device 13, and the Y-shaped rinsing liquid conduit 6' are preferably integrated together with the control unit and the data line 14 in one device.

Figure 4:
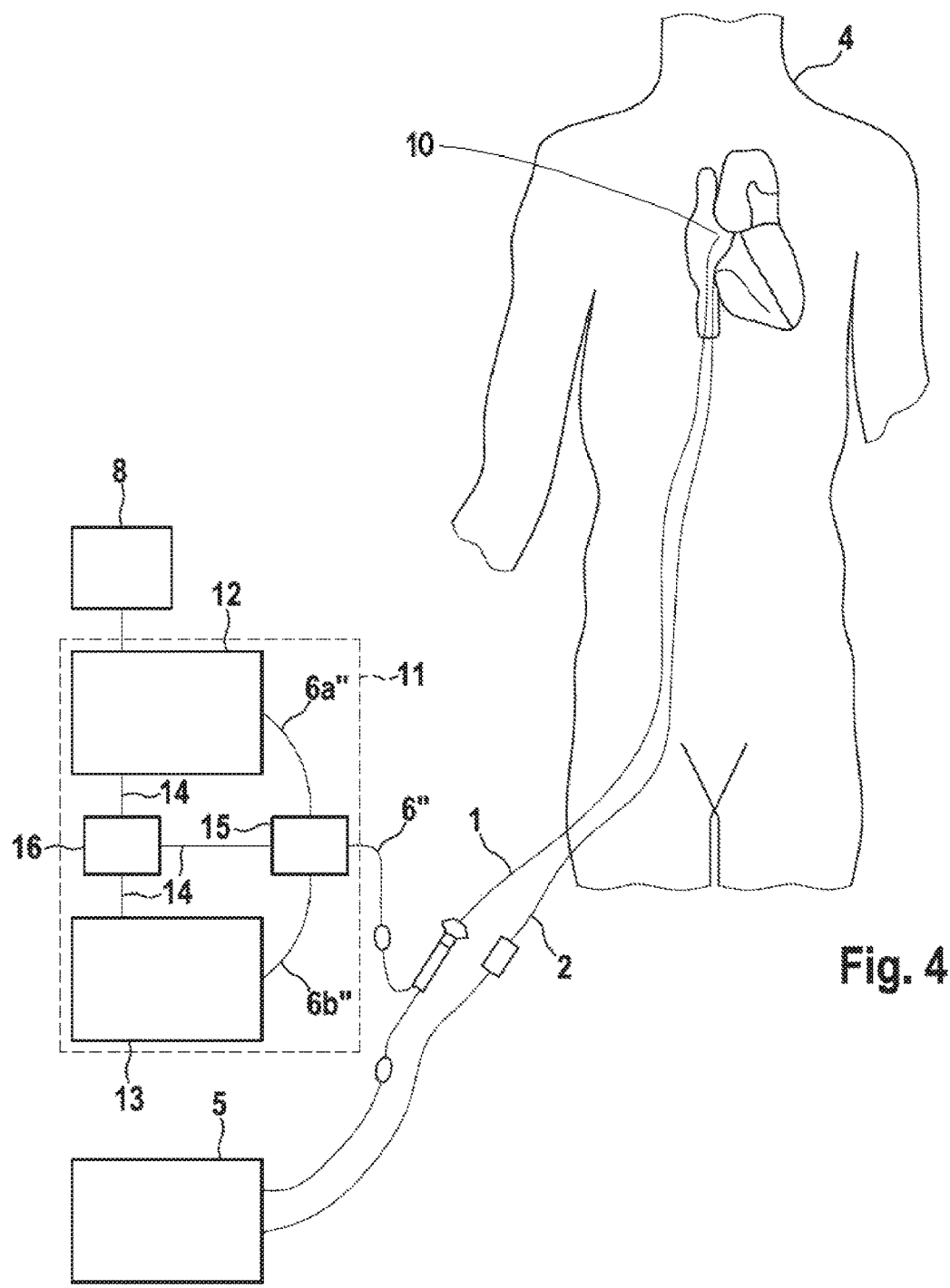
FIG. 4 shows a second version of the invention.

FIG. 4 shows another version of the invention which modifies the approach of FIG. 3. A valve 15 connects the rinsing liquid conduit 6" alternately to the pump 12 and to the blood pressure measurement device 13 via two proximal sections 6a" and/or 6b" at the proximal end of the rinsing liquid conduit 6". A control unit 16 coordinates the activity of the valve 15 with the function of the pump 12 and the blood pressure measurement device 13 via various data lines 14. The advantage of this version is the complete separation of the pump function and the blood pressure measurement, so that the former cannot interfere with the latter function.

The pump 12, the blood pressure measurement device 13, the valve 15, and the Y-shaped rinsing liquid conduit 6" are preferably integrated into one device together with the control unit 16 and the data lines 14.

Figure 5:
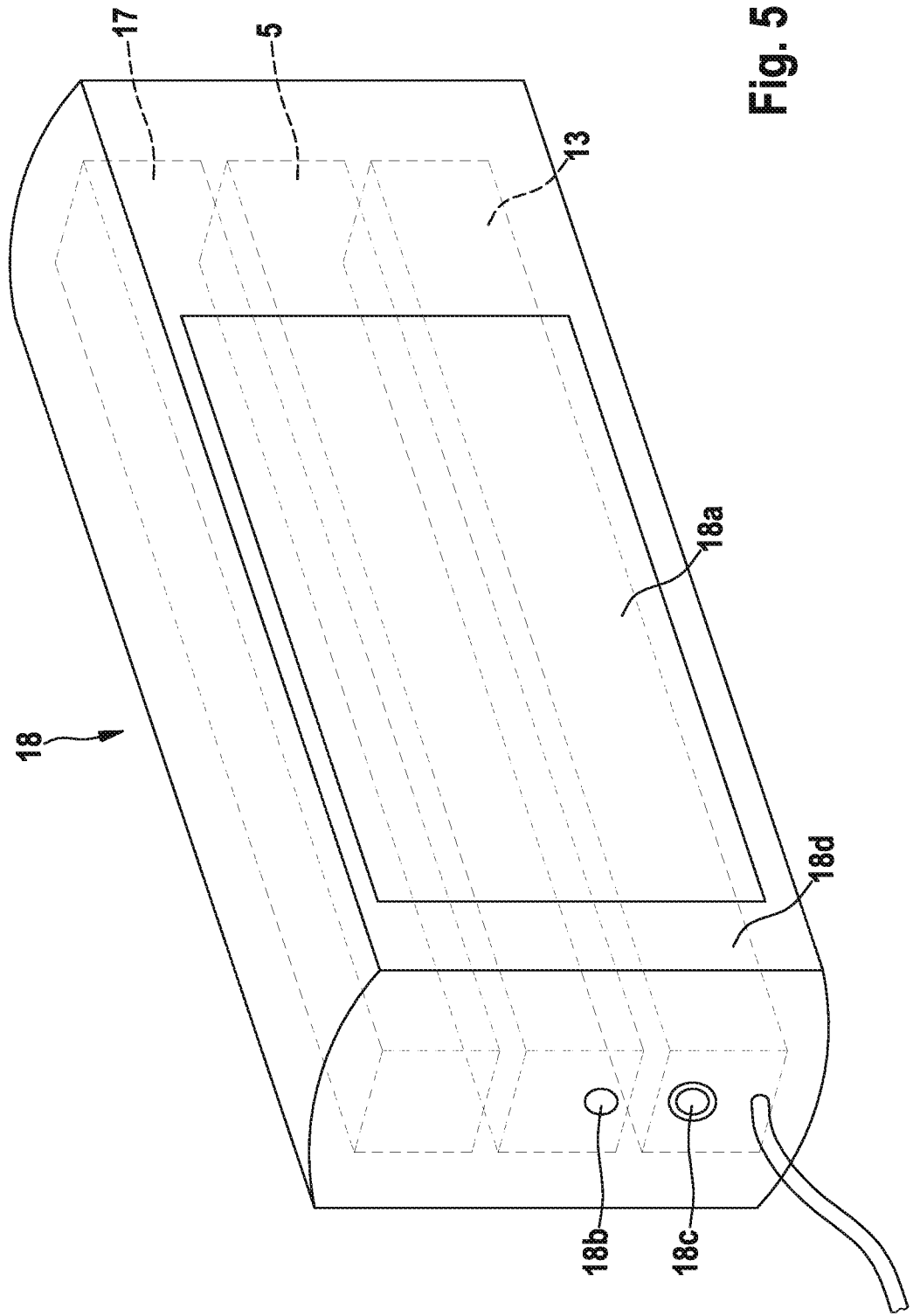
FIG. 5 shows a schematic diagram of one version of the measurement and evaluation components of the arrangement.

FIG. 5 shows a version in which an ablation evaluation unit 17 is combined with the ECG measurement device 5 as well as with the blood pressure measurement device 13 to form a measurement and evaluation device 18 having a display shield 18a. The inputs 18b and 18c of the ECG measurement device 5 and the blood pressure measurement device 13 are provided close together in the housing 18d of the combination device 18, so the feeder is lines to the two inputs from the proximal end of the ablation catheter may also be combined into one measurement tube 19 (not shown).

The invention is not intended to be limited to the exemplary versions of the invention described above, but rather is intended to be limited only by the claims set out below. Thus, the invention encompasses all different versions that fall literally or equivalently within the scope of these claims.

What is claimed is:

1. A cardiac ablation catheter system including:
   a. an ablation catheter having:
      (1) an ablation area from which ablation energy may be delivered, and
      (2) a rinsing liquid conduit opening on a rinsing aperture,
   b. an ablation generator configured to supply ablation energy to the ablation area,
   c. a rinsing liquid pump configured to supply a rinsing liquid through the rinsing liquid conduit to the rinsing aperture,
   d. a blood pressure measurement device:
      (1) in fluid communication with the rinsing liquid conduit of the ablation catheter, and
      (2) being configured to detect intracardiac blood pressure through rinsing liquid situated within the rinsing liquid conduit while the rinsing liquid pump supplies the rinsing liquid through the rinsing liquid conduit to the rinsing aperture.

2. The cardiac ablation catheter system of claim 1 wherein the ablation generator is configured to supply ablation energy to the ablation area in the form of one or more of:
   a. high-frequency voltage, and
   b. a refrigerant.

3. The cardiac ablation catheter system of claim 1 further including a supply/measurement control unit configured to meter the rinsing liquid over time from the rinsing liquid pump and through the rinsing liquid conduit.

4. The cardiac ablation catheter system of claim 1 further including a supply/measurement control unit configured to intermittently supply the rinsing liquid from the pump and through the rinsing liquid conduit over time.

5. The cardiac ablation catheter system of claim 4 wherein the supply/measurement control unit is integrated with the rinsing liquid pump.

6. The cardiac ablation catheter system of claim 4 wherein the supply/measurement control unit is integrated with the blood pressure measurement device.

7. The cardiac ablation catheter system of claim 4 wherein the supply/measurement control unit is defined by a unit separate from and connectable to the rinsing liquid pump and the blood pressure measurement device via data communication lines.

8. The cardiac ablation catheter system of claim 1 further including a branched rinsing liquid conduit simultaneously connecting:
   a. the rinsing liquid conduit of the ablation catheter,
   b. the blood pressure measurement device, and
   c. the rinsing liquid pump.

9. The cardiac ablation catheter system of claim 1 further including an ECG measurement device configured to sense cardiac action potentials at the ablation catheter.

10. The cardiac ablation catheter system of claim 9 further including an ablation evaluation unit connected to the ECG measurement device, the ablation evaluation unit being configured to indicate whether ablation is relieving cardiac arrhythmia.

11. The cardiac ablation catheter system of claim 1 further including an ablation evaluation unit connected to the blood pressure measurement device, the ablation evaluation unit being configured to indicate whether ablation is relieving cardiac arrhythmia.

12. The cardiac ablation catheter system of claim 1 wherein the blood pressure measurement device is combined with the rinsing liquid pump to define a single integrated unit.

13. A cardiac ablation catheter system including:
   a. an ablation catheter having:
      (1) an ablation area configured to deliver ablation energy to cardiac tissue, and
      (2) a rinsing liquid conduit opening at or adjacent to the ablation area;
   b. a rinsing liquid pump configured to supply a rinsing liquid through the rinsing liquid conduit,
   c. a blood pressure measurement device configured to:
      (1) measure the liquid pressure within the rinsing liquid conduit during supply of the rinsing liquid by the rinsing liquid pump, and
      (2) provide a measure of intracardiac blood pressure therefrom,
   wherein the rinsing liquid pump and blood pressure measurement device are both in simultaneous fluid communication with the rinsing liquid conduit.

14. The cardiac ablation catheter system of claim 13 wherein:
   a. the rinsing liquid pump is configured to periodically supply the rinsing liquid through the rinsing liquid conduit, and
   b. the blood pressure measurement device is further configured to measure the liquid pressure within the rinsing liquid conduit when the rinsing liquid pump is not supplying the rinsing liquid through the rinsing liquid conduit.

15. The cardiac ablation catheter system of claim 13 further including an ablation generator configured to supply ablation energy to the ablation area in the form of one or more of:
   a. high-frequency voltage, and
   b. a refrigerant.

16. The cardiac ablation catheter system of claim 13 further including an ECG measurement device configured to sense cardiac action potentials at the ablation catheter.

17. The cardiac ablation catheter system of claim 16 further including an ablation evaluation unit connected to the ECG measurement device, the ablation evaluation unit being configured to indicate whether ablation is relieving cardiac arrhythmia.

18. The cardiac ablation catheter system of claim 13 further including an ablation evaluation unit connected to the blood pressure measurement device, the ablation evaluation unit being configured to indicate whether ablation is relieving cardiac arrhythmia.

19. The cardiac ablation catheter system of claim 13 wherein the rinsing liquid pump and blood pressure measurement device are configured as a single integrated unit.

20. A cardiac ablation method including the steps of:
   a. intracardially providing an ablation catheter having:
      (1) an ablation area delivering ablation energy, and
      (2) a rinsing aperture providing a rinsing liquid from a rinsing liquid conduit supplied by a rinsing liquid pump, b. measuring intracardiac blood pressure through the rinsing liquid while the rinsing liquid pump provides rinsing liquid through the rinsing aperture.

21. The method of claim 20 further including the steps of:

a. monitoring the intracardiac blood pressure over a time period during which ablation energy is delivered, and b. providing an indication of whether ablation is relieving cardiac arrhythmia, the indication being at least partially dependent on changes in intracardiac blood pressure.

22. The method of claim 20 further including the steps of:

a. generating an ECG over a time period during which ablation energy is delivered, and b. providing an indication of whether ablation is relieving cardiac arrhythmia, the indication being at least partially dependent on changes in the ECG.

\* \* \* \* \*